United States Patent [19]

Dessau

[11] Patent Number: 4,658,045

[45] Date of Patent: Apr. 14, 1987

[54] PROCESS FOR PREPARING DISUBSTITUTED FURANS

[75] Inventor: Ralph M. Dessau, Edison, N.J.

[73] Assignee: Mobil Oil Corporation, New York, N.Y.

[21] Appl. No.: 801,180

[22] Filed: Nov. 22, 1985

[51] Int. Cl.$^4$ .......................................... C07D 307/36
[52] U.S. Cl. .................... 549/506; 549/497; 549/504
[58] Field of Search .................. 549/497, 504, 506

[56] References Cited

U.S. PATENT DOCUMENTS

| | | | |
|---|---|---|---|
| 3,702,886 | 11/1972 | Argnuer et al. | 423/328 |
| 3,709,979 | 1/1973 | Chu | 423/328 |
| 3,832,449 | 8/1974 | Rosinski et al. | 423/328 |
| 4,016,245 | 4/1977 | Plank et al. | 423/328 |
| 4,046,859 | 9/1977 | Plank et al. | 423/328 |
| 4,440,871 | 4/1984 | Lok et al. | 502/214 |

FOREIGN PATENT DOCUMENTS 764464 8/1971 Belgium.

OTHER PUBLICATIONS

Dunlop et al., The Furans, ACS Monograph Series, Reinhold Publishing Corp., New York (1953), p. 35.

*Primary Examiner*—Richard L. Raymond
*Attorney, Agent, or Firm*—Alexander J. McKillop; Michael G. Gilman; Malcolm D. Keen

[57] ABSTRACT

2,5-disubstituted furans are prepared by the cyclization of a 1,4-diketone in the presence of an intermediate or large pore sized acidic zeolite catalyst, preferably at elevated temperatures.

10 Claims, No Drawings

PROCESS FOR PREPARING DISUBSTITUTED FURANS

BACKGROUND OF THE INVENTION

1. Field of the Invention

This invention relates to a process for the preparation of 2,5-disubstituted furans.

2. Discussion of the Prior Art 2,5-Disubstituted furans have been prepared by the cyclization of various open-chain compounds. 1,4-Diketones are known to cyclize on heating with sulfuric acid in a liquid phase reaction system.

Disubstituted furans are useful as solvents and as intermediates in the preparation of insecticides and pharmaceuticals. The reaction of disubstituted furans with hydrogen sulfide at elevated temperatures in the presence of alumina provides a convenient method for making the corresponding disubstituted thiophenes.

SUMMARY OF THE INVENTION

The present invention is a process for preparing 2,5-disubstituted furans which comprises contacting a 1,4-diketone with an acidic zeolite catalyst having a Constraint Index of less than 12 at a temperature in the range about 100°–500° C.

In a more specific aspect, the present invention is a process for preparing disubstituted furans of the formula:

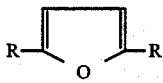

wherein each R is a lower alkyl group or a phenyl group, which comprises contacting a ketone of the formula:

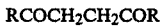

with an acidic zeolite catalyst having a Constraint Index of less than 12 at a temperature in the range about 100°–500° C.

DESCRIPTION OF THE PREFERRED EMBODIMENTS

Diketones

1–4 diketones, also known as gamma-diketones, constitute a recognized class of organic compounds, and methods for their preparation are well known to those skilled in the art.

Particularly useful in the practice of the present invention are 1,4-diketones of the formula $RCOCH_2CH_2COR$, wherein each R, individually selected, is a lower-alkyl group or a phenyl group. Particularly preferred are lower-alkyl groups having 1 to 4 carbon atoms, such as methyl, ethyl, propyl, isopropyl, butyl, isobutyl and sec-butyl. The phenyl group may bear noninterfering substituents (substituents which do not interfere with the cyclization reaction), such as lower-alkyl, halo, lower-alkoxy, etc.

Catalysts

The catalysts useful in practicing the process of the present invention are intermediate or large pore size zeolites having a Constraint Index of less than 12, generally ranging downward from 12 to 1. Particularly preferred are intermediate pore size zeolites having a Constraint Index between 2 to 12. These zeolites retain a degree of crystallinity for long periods of time, even when exposed to steam at high temperature, under conditions which would induce irreversible collapse of the framework of other zeolites, such as those of the X and A type. When reactivating these catalysts, relatively higher temperatures may be utilized to burn off the carbonaceous deposits formed during use.

An important characteristic of the crystal structure of intermediate or large pore zeolite catalysts is that they provide constrained access to, and egress from, the intracrystalline free space by virtue of having a pore dimension greater than about 5 Angstroms and pore windows of about a size such as would be provided by 10-membered rings of oxygen atoms. It is to be understood, of course, that these rings are those formed by the regular disposition of the tetrahedra making up the anionic framework of the crystalline aluminosilicate, the oxygen atoms themselves being bonded to the silicon or aluminum atoms at the centers of the tetrahedra. The preferred zeolite catalysts useful in practicing the process of this invention have a silica-to-alumina mole ratio of at least about 12, and generally higher, in addition to a structure providing constrained access to the crystalline-free space. Only sufficient alumina need be present to impart acidity to the catalyst.

The silica-to-alumina rato referred to above may be determined by conventional analysis, and the ratio is meant to represent, as closely as possible, the ratio in the rigid anionic framework of the zeolite crystal and to exclude aluminum in the binder or in cationic or other form within the channels. A simple determination of the "Constraint Index" may be made by continuously passing a mixture of an equal weight of normal hexane and 3-methylpentane over a sample of zeolite at atmospheric pressure according to the following procedure. A sample of the zeolite, in the form of pellets or extrudate, is crushed to a particle size about that of coarse sand and mounted in a glass tube. Prior to testing, the zeolite is treated with a stream of air at 1000° F. for at least 15 minutes. The zeolite is then flushed with helium and the temperature adjusted between 550° and 950° F. to give an overall hydrocarbon conversion during the test between 10 and 60%. The mixture of hydrocarbons is passed at 1 liquid hourly space velocity (i.e., 1 volume of liquid hydrocarbon per volume of zeolite per hour) over the zeolite with a helium dilution to give a helium-to-total hydrocarbon mole ratio of 4:1. After 20 minutes on stream, a sample of the effluent is taken and analyzed, most conveniently by gas chromatography, to determine the fraction remaining unconverted, i.e., uncracked, for each of the two hydrocarbons.

The "Constraint Index" is calculated as follows:

$$\text{Constraint Index} = \frac{\log_{10}(\text{fraction of n-hexane remaining})}{\log_{10}(\text{fraction of 3-methyl pentane remaining})}$$

It approximates the ratio of the cracking rate constants for the two hydrocarbons.

Constraint Index (CI) values for some typical zeolites are:

| Zeolite | CI |
| --- | --- |
| ZSM-5 | 8.3 |
| ZSM-11 | 8.7 |

-continued

| Zeolite | CI |
| --- | --- |
| ZSM-12 | 2 |
| ZSM-38 | 2 |
| ZSM-35 | 4.5 |
| TMA Offretite | 3.7 |
| Beta | 0.6 |
| ZSM-14 | 0.5 |
| H—Zeolon | 0.4 |

It is to be understood that the above Contraint Index values typically characterize the specified zeolites, but that such are the cumulative result of several variables used in determination and calculation thereof. Thus, for a given zeolite, depending on the temperatures employed within the aforenoted range of 550° to 950° F. with hydrocarbon conversion being between 10 and 60%, the Constraint Index may vary somewhat from that shown in the Table. Likewise, other variables, such as the crystal size of the zeolite, the presence of possible occluded contaminants and binders intimately combined with the zeolite, may affect the Constraint Index. It will accordingly be understood by those skilled in the art that the Constraint Index, as utilized herein, while affording a highly useful means for characterizing the zeolites of interest, is approximate, taking into consideration the manner of its determination, with probability, in some instances, of compounding variables extremes.

The class of zeolites defined herein is exemplified by ZSM-5, ZSM-11, ZSM-12, ZSM-35, ZSM-38 and other similar materials. ZSM-5 is more particularly described in U.S. Pat. No. 3,702,886. ZSM-11 is more particularly described in U.S. Pat. No. 3,709,979. ZSM-12 is more particularly described in U.S. Pat. No. 3,832,449. ZSM-35 is more particularly described in U.S. Pat. No. 4,016,245. ZSM-38 is more particularly described in U.S. Pat. No. 4,046,859.

The specific zeolites described above, when prepared in the presence of organic cations, are catalytically inactive, possibly because the intracrystalline free space is occupied by organic cations from the forming solution. They may be activated by heating in an inert atmosphere at 1000° F. for one hour, for example, followed by base-exchange with ammonium salts followed by calcination at 1000° F. in air. The presence of organic cations in the forming solution may not be absolutely essential to the formation of this type zeolite; however, the presence of these cations does appear to favor the formation of this special type of zeolite. More generally, it is desirable to activate this type catalyst by base-exchange with ammonium salts followed by calcination in air at about 1000° F. for from about 15 minutes to about 24 hours.

As used herein, the terminology "acidic zeolite catalyst" is to be broadly construed. It is inclusive of crystalline aluminosilicates and aluminosilicate-like materials, provided they have the properties discussed above, particularly large or intermediate pore size and a Constraint Index of less than 12. By way of non-limiting illustration, the aluminosilicate may be an aluminoborosilicate or include oxides of other metals, such as calcium, iron or the like. A particularly interesting class of acidic zeolite catalysts, designated silicoaluminophosphates or SAPO's, is disclosed in U.S. Pat. No. 4,440,871.

Natural zeolites may sometimes be converted to this type zeolite catalyst by one or more of various activation procedures and other treatments, such as base-exchange, steaming, alumina extraction and calcination. Natural minerals which may be so treated include ferrierite, brewsterite, stilbite, dachiardite, espistilbite, heulandite, and clinoptilolite. However, the preferred crystalline aluminosilicates for use in the process of the present invention are ZSM-5, ZSM-11, ZSM-12, ZSM-35, and ZSM-38, with ZSM-5 particularly preferred.

When synthesized in the alkali metal form, the zeolite is conveniently converted to the hydrogen form, generally by intermediate formation of the ammonium form, by ammonium ion-exchange and calcination of the ammonium form to yield the hydrogen or acid form.

In practicing the cyclization process of the invention, it may be desirable to incorporate the above-described crystalline aluminosilicate zeolite or aluminosilicate-like material in another material resistant to the temperature and other conditions employed in the process. Such matrix materials include synthetic or naturally-occurring substances, such as clays, silica and/or metal oxides. The latter may be either naturally-occurring or in the form of gelatinous precipitates or gels, including mixtures of silica and metal oxides. Naturally-occurring clays which can be composited with the zeolite include those of the montmorillonite and kaolin families, which families include the sub-bentonites and the kaolins, commonly known as Dixie, McNamee-Georgia and Florida clays, or others in which the main mineral constituent is halosite, kaolinite, dickite, nacrite or anauxite. Such clays can be used in the raw state as originally mined or initially subjected to calcination, acid treatment or chemical modification.

In addition to the foregoing materials, the zeolites employed herein may be composited with a porous matrix material, such as alumina, silica-alumina, silica-magnesia, silica-zirconia, silica-thoria, silica-beryllia, silica-titania as well as ternary compositions, such as silica-alumina-thoria, silica-alumina-zirconia, silica-alumina-magnesia and silica-magnesia-zirconia. The matrix may be in the form of a co-gel. The relative proportions of zeolite component and inorganic oxide gel matrix may vary widely, with the zeolite content ranging from between about 50 to about 99 wt %, and more, usually in the range of about 75 to 80 wt %, of the composite.

Process Conditions

Optimal yields are obtained when the reactant diketone, diluted with an inert gas, such as nitrogen, is passed over the zeolite catalyst or through a bed of the catalyst at a temperature in the range about 100°-500° C., with temperatures in the range of 250°-350° C. being particularly preferred. Cyclization will occur at temperatures below about 100°, but at a much slower rate, requiring progressively increasing contact times as the temperature is lowered or recycle of the diketone reactant to achieve desirable yields of substituted furan. On the other hand, cyclization at temperatures approaching 500° C. will be very rapid, requiring only a very brief contact time between the reactant diketone and the zeolite catalyst, but decomposition or polymerization reactions affecting catalyst activity become more troublesome at temperatures above about 500° C. As will be apparent, the temperature selected will depend in part on the activity and/or acidity of the catalyst utilized and the time the diketone remains in contact with the catalyst. Effecting the reaction at a temperature in the range of about 250°-350° C. provides rapid cyclization and a high yield of disubstituted furan with minimal risk of it being decomposed. It is important to note that no significant amount of cyclization occurs in the absence of a catalyst.

The invention is further illustrated by means of the following non-limiting examples, in which all percentages are by weight, unless the contrary is stated.

In the experimental procedure utilized, cyclization was effected in a downflow gas reactor containing the zeolite catalyst. The reactant diketone was fed by means of a Sage syringe pump in a stream of nitrogen. The reactor effluent was collected in a chilled vessel and then analyzed on a 12 meter 3% SE-30 capillary column at 60° C. The reactants and products were identified by comparison of retention times on two different columns with those of authentic samples, and by GC-MS analysis on a Hewlett-Packard 5992 instrument.

EXAMPLE 1

Acetonylacetone, at a feed rate of 2.2 ml per hour in a stream of nitrogen, flowing at the rate of 89 cc/min, was passed through the reactor containing 204 mg of ZSM-5 in acid form. The catalyst had a silica-to-alumina ratio of 70:1 and an alpha of 278. Two runs at 300° C. gave a 98.3% yield of 2,5-dimethylfuran. About 1.0% of 3-methyl-2-cyclopenten-1-one was obtained as a by-product.

EXAMPLE 2

Acetonylacetone, at a feed rate of 2.2 ml per hour, in a stream of nitrogen, flowing at the rate of 46 cc/min, was passed through the reactor containing 1.04 g of ZSM-5 having a silica to alumina ratio of 300:1 in acid form at 350° (the zeolite catalyst was preheated to 500° C. prior to starting the reaction). Samples were collected over the periods of the time indicated and analyzed with the results shown below:

| Sample | Time in Mins. | Acetonyl-acetone | By-Product | Dimethylfuran |
|---|---|---|---|---|
| A | 20–60 | 0.3% | 2.8% | 92.7% |
| B | 60–120 | 0.2% | 2.2% | 96.1% |
| C | 120–180 | 0.1% | 1.9% | 96.4% |
| D | 180–270 | 0.1% | 1.7% | 97.1% |
| E | 270–345 | 0.1% | 1.6% | 97.3% |
| F | 345–395 | 0.1% | 1.5% | 97.6% |

The by-product, as in Example 1, was 3-methyl-2-cyclopenten-1-one.

Similar results are obtained when 2,5-diphenylfuran is prepared starting with 1,2-dibenzoylethane, and when 2-methyl-5-ethylfuran is prepared by the cyclization of 1-acetyl-2-propionylethane. Obviously, the nature of the by-product resulting, particularly the 3-substituent thereof, will, like the product, derive from the R substituents in the diketone reactant.

EXAMPLE 3

This example illustrates the effect of reaction temperature on yield.

Acetonylacetone was fed to the reactor at the rate of 2.0 ml per hour in a stream of nitrogen, flowing at the rate of 20 cc/min. The reactor contained 502 mg of acid form ZSM-5, the same type as used in Example 1. Samples were collected during the course of the run and analyzed, with the results shown below:

| Sample | T °C. | Acetonylacetone | Dimethylfuran |
|---|---|---|---|
| A | 250 | 1.2% | 97.6% |
| B | 250 | 9.9% | 89.0% |
| C | 225 | 75.0% | 24.0% |
| D | 225 | 77.6% | 21.8% |
| E | 225 | 80.0% | 19.1% |
| F | 225 | 77.7% | 21.5% |

It should be noted that, while the degree of conversion falls off markedly when the reaction is lowered from 250° to 225° C., about 20–25% of the acetonylacetone fed is cyclized. Unreacted diketone is not appreciably degraded or converted to undesirable by-products, and can be recovered and/or recycled.

The following Table illustrates the high rate of conversion and good yields of product obtained by operation in the preferred 250°–350° C. temperature range. Acetonylacetone was fed at the rate of 2.0 or 2.2 ml per hour in a stream of nitrogen flowing at the rate of 45 cc/min.

| T °C. | Time in Mins. | % Conversion | % Yield |
|---|---|---|---|
| 250 | 15–75 | 98.1 | 97.6 |
| 250 | 76–105 | 90.1 | 89.0 |
| 350 | 60–120 | 99.8 | 96.1 |
| 350 | 345–395 | 99.9 | 97.6 |

In the Table, T°C. is the reaction temperature, time is the time span in minutes during a particular reaction run, wherein the amounts of acetonylacetone fed and 2,5-dimethylfuran recovered are measured. % Conversion is the amount of acetonylacetone consumed in the reaction and % yield is the yield of 2,5-dimethylfuran obtained. The % yield is slightly less than the % conversion, the difference being the amount of 3-methyl-2-cyclopent-en-1-one by-product formed. A different and more acidic ZSM-5 zeolite catalyst was used in the 250° C. temperature runs than was used in the 350° temperature runs.

I claim:

1. A process for preparing 2,5-disubstituted furans, which comprises contacting a 1,4-diketone with an acidic zeolite catalyst having a Constrant Index less than 12 at a temperature in the range about 100°–500° C.

2. A process for preparing disubstituted furans of the formula:

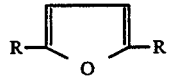

wherein each R is an alkyl group or a phenyl group, which comprises passing a diketone of the formula:

RCOCH$_2$CH$_2$COR over an acidic zeolite catalyst having a Constraint Index less than 12 at a temperature in the range about 100°–500° C.

3. A process according to claim 2, wherein the zeolite catalyst has a silica to alumina ratio of at least 12:1.

4. A process according to claim 3, wherein the Constraint Index is between about 2 to 12.

5. A process according to claim 4, wherein the zeolite catalyst is ZSM-b 5, ZSM-11, ZSM-12, ZSM-35 or ZSM-38.

6. A process according to claim 5, wherein the zeolite catalyst is ZSM-5.

7. A process according to claim 2, wherein the temperature is in the range of about 250°–350° C.

8. A process according to claim 2, wherein the diketone is diluted with an inert gas.

9. A process according to claim 8, wherein the inert gas is nitrogen.

10. A process according to claim 2, wherein the diketone is acetonylacetone.

* * * * *